US00PP27684P3

(12) United States Plant Patent
Fretwell

(10) Patent No.: US PP27,684 P3
(45) Date of Patent: Feb. 21, 2017

(54) ***CLEMATIS* PLANT NAMED 'BFCCDEL'**

(50) Latin Name: *Clematis lanuginosa×patens*
Varietal Denomination: BFCCDEL

(71) Applicant: Barry Fretwell, Exeter (GB)

(72) Inventor: Barry Fretwell, Exeter (GB)

( * ) Notice: Subject to any disclaimer, the term of this patent is extended or adjusted under 35 U.S.C. 154(b) by 63 days.

(21) Appl. No.: 14/545,364

(22) Filed: Apr. 27, 2015

(65) Prior Publication Data

US 2016/0316603 P1 Oct. 27, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — Keith Robinson
(74) *Attorney, Agent, or Firm* — Cassandra Bright

(57) ABSTRACT

A new and distinct *Clematis* hybrid named 'BFCCDEL' is disclosed, characterized by a distinctive double or semi-double creamy yellow to pale yellow flowers. Plants have a dense, shrubby plant form and are well suited for container plantings. Flowers are produced from May/June through August/September. The new cultivar is a *Clematis* typically suited for ornamental container and landscape use.

1 Drawing Sheet

Latin name of the genus and species: *Clematis lanuginosa×patens*.
Variety denomination: 'BFCCDEL'.

BACKGROUND OF THE INVENTION

The new cultivar is the result of planned breeding program, conductor by the inventor, Barry Fretwell in Exeter, Great Britain. The seed parent is an unpatented, proprietary *Clematis lanuginosa* referred to as 'P-3-833'. The pollen parent is an unpatented, proprietary *Clematis patens* referred to as 'P-7-13'. The cross was made during 2006 and the selection of the new variety was made in 2009.

After selecting and isolating the new cultivar, asexual reproduction of the new cultivar 'BFCCDEL' was first performed in in Exeter, Great Britain at a nursery by vegetative cuttings in 2010. 'BFCCDEL' has since produced multiple generations, and has shown that the unique features of this cultivar are stable and reproduced true to type.

SUMMARY OF THE INVENTION

The cultivar 'BFCCDEL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BFCCDEL'. These characteristics in combination distinguish 'BFCCDEL' as a new and distinct *Clematis* cultivar:

1. Double flowers, and semi double flowers.
2. Creamy yellow to pale yellow flowers.
3. Flowering from May/June through August/September.
4. Small foliage size.
5. Suitability for container culture.

PARENTAL COMPARISON

Plants of the new cultivar 'BFCCDEL' are similar to the seed parent variety in most horticultural characteristics. However, the new variety differs from the seed parent in the following:

1. Flowers of the parent variety are more pure white, compared to cream/yellow flowers of the new variety.
2. The new variety has smaller foliage.
3. The new variety has a plant habit better suited for containers.

Plants of the new cultivar differ from the pollen parent in the following:

1. The pollen parent has semi-double pale yellow flowers, comparator flowers are lighter in color, with less coloration.
2. The new variety produces fully double and semi-double flowers, the pollen parent produces semi-double flowers.
3. The new variety has smaller foliage.

COMMERCIAL COMPARISON

Plants of the new cultivar 'BFCCDEL' are similar to the commercial variety *Clematis* hybrid 'Duchess of Edinburgh', unpatented, in most horticultural characteristics. However, the new variety differs from 'Duchess of Edinburgh' in the following:

1. The new variety produces cream/yellow flowers, compared to the white flowers of this comparator.
2. The new variety has a plant habit better suited for containers.
3. Plants of the new variety have a lighter green leaf color
4. Plants of the new variety have a shorter internode space, creating a shrubbier plant form.

The new variety can also be compared to *Clematis patens* 'Yuki Okoshi', unpatented, differing in the following characteristics:

1. The new variety produces cream/yellow flowers, compared to the white flowers of this comparator.
2. The new variety has a plant habit better suited for containers.
3. Foliage of the new variety is smaller.

4. Plants of the new variety have a shorter internode space, creating a shrubbier plant form.

BRIEF DESCRIPTION OF THE PHOTOGRAPH

The accompanying photograph in FIG. 1 illustrates in full color a typical mature flowers and foliage of 'BFCCDEL' grown outdoors in Germany. Age of the plant is approximately 8 months. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'BFCCDEL' plants grown outdoors in Germany. The growing temperature ranged from 0° C. to 25° C. at night to 0° C. to 30° C. during the day. No artificial light, photoperiodic treatments or chemical treatments were given to the plants. Plants were pinched twice. Measurements and numerical values represent averages of typical flowering types.

Botanical classification: *Clematis lanuginosa×patens* 'BFCCDEL'.

Age of the plant described: Approximately 8 months.

Container size of the plant described: Growing in the ground.

PROPAGATION

Typical method: Vegetative cuttings.

Time to initiate root developments: 22 days in the summer at 24° C.

Time to produce a rooted cutting/young plant: 40-50 days in the summer at 20° to 26° C.

Root description: Fine, fibrous.

PLANT

Growth habit: Shrubby, climbing vine.

Time to produce a finished flowering plant: Approximately 12 to 14 months from an unrooted cutting to a deliverable plant, in a 1.5 or 2 Liter size container.

Height: Approximately 8 to 10 feet, measured from the soil line of the ground after approximately 8 months.

Plant spread: Approximately 2 to 2.5 feet.

Growth rate: Rapid during active growing season in Spring. 40 to 50 cm per month.

Branching characteristics: One main stem, easily making side branches from a pinch. Typically 3 to 5 main lateral branches form from a pinch.

Length of main stem: Approximately 200 to 300 cm.

Diameter of main stem: Approximately 0.2 cm.

Main stem color: Near RHS Green 143C, flushed with Greyed-Red 178C.

Main stem texture: Glabrous.

Internode length: Varies from 8 to 12 cm.

Strength: Strong, flexible, semi-woody.

FOLIAGE

Leaf:

*Arrangement*.—Opposite, Ternate and simple leaves present.

*Leaves per lateral branch*.—Average range 3.

*Ternate leaf*.—Average Length: approximately 14 to 21 cm. Average Width: approximately 10 to 14 cm.

*Leaflets and single leaves*.—Average Length: approximately 4 to 7 cm. Average Width: approximately 3 to 4 cm. Shape of blade: Cordate. Apex: Acute. Base: Obtuse. Attachment: Stalked. Margin: Entire. Texture upper and lower surfaces: Glabrous. Color: Young foliage upper side: Near RHS Green 143C. Young foliage under side: Near RHS Yellow-Green 144B. Mature foliage upper side: Near. RHS Green 137A. Mature foliage under side: Near RHS Green 143B. Venation: Type: Pinnate. Venation color upper side: Near RHS Yellow-Green 144B. Venation color under side: Near RHS Yellow-Green 144B.

Petiole:

*Length*.—Approximately 4.0 to 6.0 cm.

*Diameter*.—Approximately 0.15 cm.

*Texture*.—Smooth.

*Color*.—Near RHS Green 143C, flushed with Greyed-Red 178B and 178C.

FLOWER

Bloom period:

*Natural season*.—May/June through August/September.

Inflorescence type and habit: Double or semi-double, axillary. Solitary occurring, rotate. Flowers facing outward. Flowering occurring on both previous year's growth and current year's growth.

Quantity of flowers and buds on the plant at a given time: 20 to 60.

Rate of flower opening: Approximately 16 days from bud to fully opened flower.

Flower longevity on plant: Approximately 10 to 14 days, after fully opened. Self-cleaning.

Inflorescence size:

*Diameter*.—Approximately 10.0 to 14.0 cm.

*Depth*.—Approximately 6.0 cm.

Flowers:

*Corolla*.—Tepal arrangement: Multi-whorled, slightly upwardly cupped. Quantity: Typically 30 to 50 per flower. Size: Length: Approximately 5.0 to 6.0 cm. Width: Approximately 0.8 to 1.0 cm. Shape: Oblong. Margin: Very slightly undulating, entire. Apex: Short acuminate. Base: Blunt. Texture: Smooth, upper and lower surfaces.

*Color*.—Tepals: When opening: Upper surface: Near RHS Yellow-White 158D, center Yellow 3A. Mid vein Green 143C. Lower surface: Near RHS Green-White 157D, center Green-Yellow 1C. Mid vein Green 143C. Fully opened: Upper surface: Near RHS Green-White 157D, center faintly flushed Yellow 2C. Mid vein faintly Green 143C. Apex flushed near Red-Purple 58A. Lower surface: Near RHS Green-White 157D, center faintly flushed Yellow 2C. Mid vein faintly Green 143C. Ageing: Upper surface: Near RHS White 155A. Mid vein very faintly Green 143C. Apex and upper margins flushed near Red-Purple 59D. Lower surface: Near RHS White 155A, apex and upper margins flushed near Red-Purple 59D.

Bud:

*Shape*.—Conical.

*Length*.—Approximately 3.7 cm.

*Diameter*.—Approximately 2.5 cm.

*Color*.—Near RHS Yellow-white 158D, flushed Yellow 2D.

Peduncles:

*Length*.—Average range 8 to 10 cm.

*Width*.—Approximately 0.3 cm.

*Angle*.—Average 90°.

*Strength*.—Flexible.

*Color*.—Near RHS Greyed-Orange 172B.

Fragrance: None.

REPRODUCTIVE ORGANS

Stamens:

*Number*.—Average 80 to 100 per flower.

*Stamen color*.—Near Yellow 7A.

*Stamen length*.—Approximately 1.8 cm.

*Anther length*.—Approximately 0.08 to 0.12 cm.

*Anther color*.—Near RHS Yellow 12B.

*Anther shape*.—Oblong.

*Pollen quantity*.—Moderate.

*Pollen color*.—Near Yellow 2A.

Pistil:

*Pistil quantity*.—40 to 60 per flower.

*Length*.—Approximately 0.8 cm.

*Style length*.—Approximately 0.7 cm.

*Style color*.—Near RHS 2D.

*Stigma*.—Shape: Linear. Color: Near RHS Yellow 2C.

OTHER CHARACTERISTICS

Seeds and fruits: Not observed to date.

Disease/pest resistance: Neither resistance nor susceptibility to normal pests of *Clematis* has been observed. Better resistance for mildew diseases of *Clematis* has been observed. The most common known mildew pathogen is *Erysiphe aquilegiae*.

Temperature tolerance: Tolerates temperatures from approximately −25° C. to 45° C.

What is claimed is:

1. A new and distinct cultivar of *Clematis* hybrid plant named 'BFCCDEL' as herein illustrated and described.

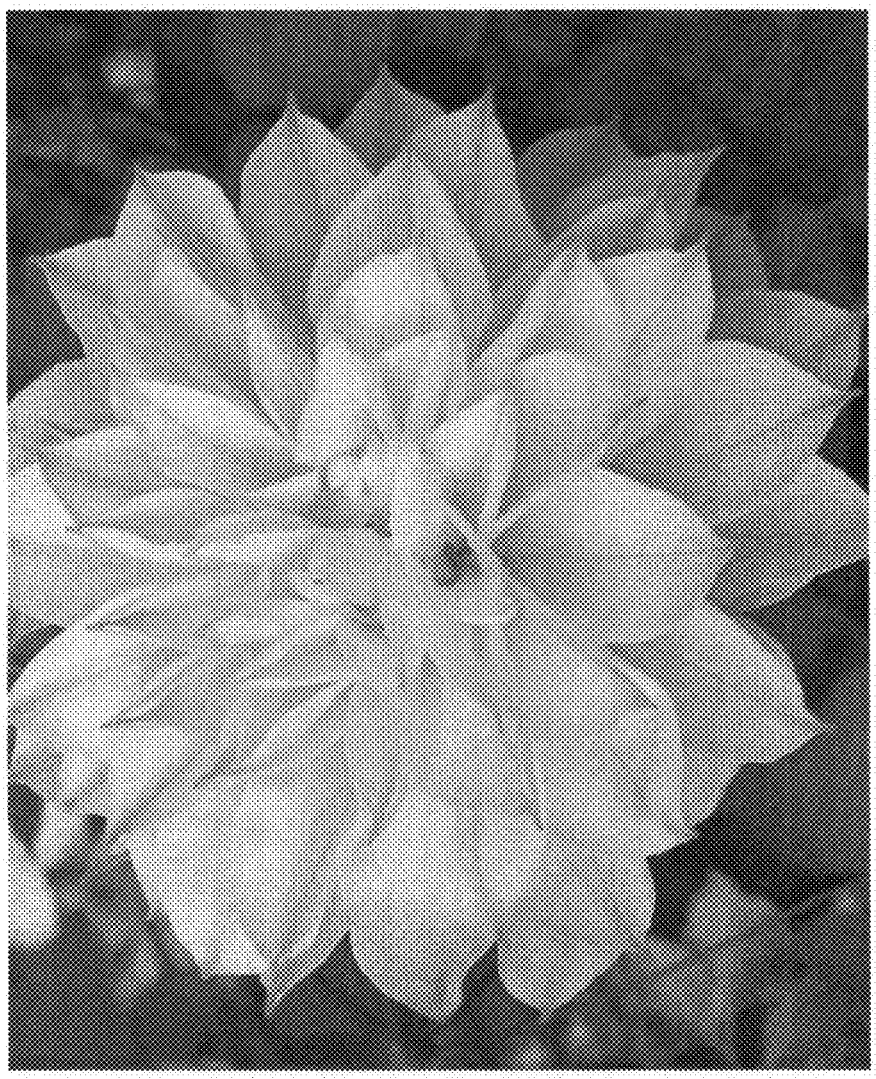

* * * * *